(12) United States Patent
Wolfinbarger, Jr.

(10) Patent No.: US 6,916,910 B2
(45) Date of Patent: *Jul. 12, 2005

(54) METHOD AND PROCESS FOR THE PRODUCTION OF COLLAGEN PREPARATIONS FROM INVERTEBRATE MARINE ANIMALS AND COMPOSITIONS THEREOF

(75) Inventor: Lloyd Wolfinbarger, Jr., Norfolk, VA (US)

(73) Assignee: Bioscience Consultants, Norfolk, VA (US)

( * ) Notice: Subject to any disclaimer, the term of this patent is extended or adjusted under 35 U.S.C. 154(b) by 215 days.

This patent is subject to a terminal disclaimer.

(21) Appl. No.: 09/999,262

(22) Filed: Nov. 28, 2001

(65) Prior Publication Data

US 2002/0147154 A1 Oct. 10, 2002

Related U.S. Application Data

(63) Continuation of application No. 08/959,272, filed on Oct. 28, 1997, now Pat. No. 6,337,389, which is a continuation-in-part of application No. 08/405,979, filed on Mar. 17, 1995, now Pat. No. 5,714,582.

(51) Int. Cl.[7] ........................... A61K 38/17; A61K 7/06; C07K 1/00
(52) U.S. Cl. ......................... 530/356; 530/402; 424/61; 424/63; 424/64; 424/70.1; 424/70.6; 424/73; 424/400; 424/401; 514/844; 514/845; 514/846; 514/847
(58) Field of Search ................ 530/356, 402; 424/61, 63, 64, 70.1, 70.6, 73, 400, 401; 514/844, 845, 846, 847

(56) References Cited

U.S. PATENT DOCUMENTS

| | | | |
|---|---|---|---|
| 2,119,822 A | 6/1938 | Mayehara ........................ 99/15 |
| 2,920,000 A | 1/1960 | Hochstadt et al. ........... 106/161 |
| 2,934,446 A | 4/1960 | Highberger et al. ........ 106/165 |
| 2,934,447 A | 4/1960 | Highberger et al. ........ 106/155 |
| 3,014,024 A | 12/1961 | Leiberman et al. ......... 260/117 |
| 3,034,852 A | 5/1962 | Nishihara ........................ 18/54 |
| 3,121,049 A | 2/1964 | Nishihara ........................ 195/6 |
| 3,131,130 A | 4/1964 | Oneson ........................... 195/6 |
| 3,303,038 A | 2/1967 | Klevens ....................... 106/155 |
| 3,314,861 A | 4/1967 | Tadahiko ........................ 196/6 |
| 3,491,760 A | 1/1970 | Bernhard ...................... 128/334 |
| 3,530,037 A | 9/1970 | Nishihara ........................ 195/6 |
| 3,562,820 A | 2/1971 | Braun .............................. 3/1 |
| 3,563,228 A | 2/1971 | Selderman ..................... 128/1 |
| 3,632,350 A | 1/1972 | Battista .......................... 99/1 |
| 3,634,561 A | 1/1972 | Hawkins et al. ............... 264/40 |
| 3,873,749 A | 3/1975 | Carpenter et al. ........... 426/350 |
| 3,894,132 A | 7/1975 | Daniel .......................... 264/138 |
| 3,917,816 A | 11/1975 | Yueh ............................ 424/61 |
| 3,949,073 A | 4/1976 | Daniels et al. ............... 424/177 |
| 4,002,739 A | 1/1977 | Turner et al. ................ 424/177 |
| 4,021,522 A | 5/1977 | Daniel .......................... 264/138 |
| 4,130,555 A | 12/1978 | Ohtsuka et al. ............. 260/117 |
| 4,140,537 A | 2/1979 | Luck et al. ................... 106/155 |
| 4,184,360 A | 1/1980 | Vadnay et al. .................. 73/28 |
| 4,233,360 A | 11/1980 | Luck et al. ................... 428/310 |
| 4,268,131 A | 5/1981 | Miyata et al. ................ 351/160 |
| 4,295,894 A | 10/1981 | Cioca et al. .................. 106/155 |
| 4,350,629 A | 9/1982 | Yannas et al. ............... 260/123 |
| 4,391,749 A | 7/1983 | Engvall et al. .............. 260/123 |
| 4,407,829 A | 10/1983 | Sjolander ...................... 426/59 |
| 4,409,332 A | 10/1983 | Jefferies et al. .............. 435/188 |
| 4,424,208 A | 1/1984 | Wallace et al. .............. 424/177 |
| 4,440,750 A | 4/1984 | Glowacki et al. ............ 424/95 |
| 4,451,397 A | 5/1984 | Huc et al. .................... 260/123 |
| 4,488,894 A | 12/1984 | Silorski et al. ................ 71/87 |
| 4,488,911 A | 12/1984 | Luck et al. ................... 106/161 |
| 4,505,817 A | 3/1985 | Blomback et al. .......... 210/484 |
| 4,505,855 A | 3/1985 | Bruns et al. ................. 260/123 |
| 4,542,014 A | 9/1985 | Bresak et al. ................ 424/70 |
| 4,557,764 A | 12/1985 | Chu ............................. 106/161 |
| 4,563,350 A | 1/1986 | Nathan et al. ................ 424/95 |
| 4,582,640 A | 4/1986 | Smestad et al. ............. 260/123 |
| 4,600,533 A | 7/1986 | Chu ............................. 530/356 |
| 4,621,631 A | 11/1986 | Paques et al. ............... 128/156 |
| 4,642,117 A | 2/1987 | Nguyen et al. .............. 623/11 |
| 4,655,980 A | 4/1987 | Chu ............................. 264/102 |
| 4,689,399 A | 8/1987 | Chu ............................. 530/356 |
| 4,703,108 A | 10/1987 | Silver et al. ................. 530/356 |
| 4,725,671 A | 2/1988 | Chu et al. .................... 530/356 |
| 4,743,229 A | 5/1988 | Chu ............................. 604/82 |
| 4,770,872 A | 9/1988 | Hsiung et al. ................ 424/71 |
| 4,774,227 A | 9/1988 | Piez et al. .................... 514/21 |
| 4,776,890 A | 10/1988 | Chu ............................. 106/161 |
| 4,789,663 A | 12/1988 | Wallace et al. .............. 514/21 |
| 4,795,467 A | 1/1989 | Piez et al. .................... 623/16 |
| 4,801,299 A | 1/1989 | Brendel et al. ............... 623/1 |
| 4,803,075 A | 2/1989 | Wallace et al. .............. 424/423 |
| 4,837,285 A | 6/1989 | Berg et al. ................... 530/356 |
| 4,847,049 A | 7/1989 | Yamamoto ..................... 422/24 |
| 4,851,513 A | 7/1989 | Devore et al. ............... 530/356 |

(Continued)

OTHER PUBLICATIONS

Miura et al., The Journal of Biological Chemistry, vol. 260, No. 28, pp. 15352–15356, 1985.*

(Continued)

*Primary Examiner*—Jon Weber
*Assistant Examiner*—Abdel A. Mohamed
(74) *Attorney, Agent, or Firm*—W. Jackson Matney, Jr.; Baker & McKenzie LLP

(57) ABSTRACT

The present invention relates to a process for the production of marine invertebrate type V telopeptide containing collagen preparations from marine invertebrates, compositions containing preparations, and methods of using these preparations. The collagen preparation includes telopeptide containing and optionally invertebrate atelopeptide containing, type V fibrillar collagen. The present collagen preparations may be employed in a variety of products including for example, cosmetic, pharmacological, dental, and cell culture products.

29 Claims, No Drawings

U.S. PATENT DOCUMENTS

| | | | |
|---|---|---|---|
| 4,861,714 A | 8/1989 | Dean, Jr. et al. | 435/68 |
| 4,863,732 A | 9/1989 | Nathan et al. | 424/95 |
| 4,863,856 A | 9/1989 | Dean, Jr. et al. | 435/68 |
| 4,865,602 A | 9/1989 | Smestad et al. | 623/16 |
| 4,867,966 A | 9/1989 | Grollier et al. | 424/71 |
| 4,883,366 A | 11/1989 | Dohi et al. | 374/184 |
| 4,883,864 A | 11/1989 | Scholz | 530/356 |
| 4,906,460 A | 3/1990 | Kim et al. | 424/70 |
| 4,931,546 A | 6/1990 | Tardy et al. | 530/356 |
| 4,950,483 A | 8/1990 | Ksander et al. | 424/422 |
| 4,980,403 A | 12/1990 | Bateman et al. | 524/17 |
| 4,983,721 A | 1/1991 | Davison | 530/356 |
| 5,001,169 A | 3/1991 | Nathan et al. | 523/113 |
| 5,024,841 A | 6/1991 | Chu et al. | 424/422 |
| 5,035,896 A | 7/1991 | Apfel et al. | 424/456 |
| 5,036,716 A | 8/1991 | Daniehl | 623/16 |
| 5,043,426 A | 8/1991 | Goldstein | 530/356 |
| 5,093,474 A | 3/1992 | Grossman et al. | 530/355 |
| 5,110,604 A | 5/1992 | Chu et al. | 424/484 |
| 5,123,925 A | 6/1992 | Smestad et al. | 623/16 |
| 5,128,136 A | 7/1992 | Bentley et al. | 424/443 |
| 5,138,030 A | 8/1992 | Pachence | 530/356 |
| 5,162,114 A | 11/1992 | Kuberasampath et al. | 424/423 |
| 5,162,506 A | 11/1992 | Hadden | 530/412 |
| 5,171,574 A | 12/1992 | Kuberasampath et al. | 424/423 |
| 5,219,576 A | 6/1993 | Chu et al. | 424/484 |
| 5,231,169 A | 7/1993 | Constantz et al. | 530/356 |
| 5,246,451 A | 9/1993 | Trescony et al. | 623/1 |
| 5,246,457 A | 9/1993 | Piez et al. | 623/16 |
| 5,264,214 A | 11/1993 | Rhee et al. | 424/422 |
| 5,304,595 A | 4/1994 | Rhee et al. | 525/54 |
| 5,316,942 A | 5/1994 | Fink | 435/273 |
| 5,331,092 A | 7/1994 | Huc et al. | 530/356 |
| 5,332,475 A | 7/1994 | Mechanic | 204/157 |
| 5,344,917 A | 9/1994 | Furukawa et al. | 530/356 |
| 5,714,582 A | 2/1998 | Wolfinbarger | 530/356 |

OTHER PUBLICATIONS

Sato et al. J. Agric. Food Chem., vol. 42, No. 3, pp. 675–676, 1994.

Sato et al. J. Agric. Food Chem., vol. 39, No. 7, pp. 1222–1225, 1991.

Sato et al. Journal of Food Science, vol. 54, No. 6, pp. 1511–1514, 1989.

Kimura, S. et al., Collagen as the Major Edible Component of Jellyfish (Stompolophus nomural), Journal of Food Science 48:1758–1760 (1983).

Hsieh, P. et al., Potential of Utilizing Jellyfish as Food in Western Countries, Trands in Food Science & Technology 5(7):225–226 (1994).

* cited by examiner

METHOD AND PROCESS FOR THE PRODUCTION OF COLLAGEN PREPARATIONS FROM INVERTEBRATE MARINE ANIMALS AND COMPOSITIONS THEREOF

This application is a continuation application of U.S. patent application Ser. No. 08/959,272 filed Oct. 28, 1997, now U.S. Pat. No. 6,337,389, which is a continuation-in-part of U.S. patent application Ser. No.08/405,979 filed Mar. 17, 1995, now U.S. Pat. No. 5,714,582, the disclosures of which are incorporated by reference in their entirety.

FIELD OF THE INVENTION

This invention relates to the method and process for the production of collagen preparations from invertebrate marine animals including jellyfish and compositions of these preparations. These collagen preparations are useful in a variety of applications ranging from medical, pharmacological, and cosmetic. The composition is available as a mixture in a gel state, in a freeze-dried state, in a salt-reprecipitated state, and can be delivered as a mixture in a fluidized state, as a mixture in a gel state, and/or in association with surfactant/detergent combinations as an intact collagen molecule or as a hydrolyzed collagen product. The process for the production of collagen from invertebrate marine sources including jellyfish, takes advantage of the physical and chemical characteristics of jellyfish where the jellyfish is essentially a gelatinous state of collagen in water surrounding simple digestive systems and attached to other collagenous structures generally described as tentacles which are used in the capture of prey for the purpose of feeding.

BACKGROUND OF THE INVENTION

The term jellyfish refers to hundreds of species of primitive marine animals belonging to the class Scyphozoa, phylum Coelenterata. Coelenterata is a phylum name derived from the Greek words meaning "hollow gut". It refers to important attributes of a group of invertebrate animals, called coelenterates, having a single internal cavity for digestion and excretion. Jellyfish often become abundant in coastal areas, particularly in late summer, and are regarded as a nuisance. Jellyfish sting swimmers, clog nuclear power plants, and fishing boat nets and, at times can cause severe damage to fishing nets owing to their huge volume and weight. In the water they are beautiful, colorful, and diaphanous creatures, yet most people only see them as a washed-up blob on the beach. Jellyfish can be found in both tropical and temperate waters of the world. The environmental factors affecting the occurrence of jellyfish are temperature, oxygen, salinity, and predation. Some species of jellyfish have great commercial potential. For example, the US coastal waters of the Florida Panhandle and all of the northern Gulf of Mexico provide an ideal environment for the seasonal proliferation of *Stomolopus meleagris*, which is commonly called the cannon-ball jellyfish. This species is found in abundance in certain areas of the world For instance, it occurs from Southern New England, USA, to Venezuela and the Gulf of Mexico. One swarm observed at Port Arkansas, Tex., USA was estimated to have drifted through the channel at a rate of approximately 2 million per hour. Jellyfish occur world-wide, being caught in the Indian, Northwest Pacific and Western Central Pacific Oceans by Far Eastern countries including Thailand, Indonesia, Malaysia, the Philippines and China. In 1991, for example, the world harvest of jellyfish was 126,419 tons and Japanese buyers pay up to $25.00 per kilogram for large processed Grade "A" *Rhopilema esculenta* jellyfish.

Fresh jellyfish contain approximately 95 to 98% water by weight, depending on the particular species and approximately 2 to 3% salt by weight, which is in approximate osmotic equilibrium with salt water. The contents of solids other than salt is extremely low; not much higher than 1% by weight. Protein content is approximately 1.3%. The lipid content of jellyfish is very low. On a wet-weight basis, lipid contents in the range 0.0046 to 0.2% have been reported. The nonpolar lipids of lyophilized jellyfish comprised 31.1% of the total lipids and sterols may account for approximately 47.8% of the nonpolar lipids. The cholesterol content of four species of coelenterates was in the range of 72.2 to 88.8% of the sterol content. Calculated from the above values, the cholesterol content on a wet-weight basis would be less than 0.35 mg/100 gm. Commercially available processed jellyfish contain approximately 5.5% protein, 25% salt and 68% water, however this type of jellyfish would be for consumption and would need to be desalted prior to consumption. As a food-stuff, the protein content of jellyfish in terms of protein level is similar to foods such as pasta and boiled rice.

Jellyfish proteins consist almost entirely of collagen. Analysis of the amino acid composition of mesogloea hydrolysate showed that glycine is the most abundant amino acid, and that hydroxyproline and hydroxy lysine, which are characteristic of collagen, are present. Tryptophan is almost totally absent. Thus, mesogloea contain proteins belonging to the collagen group.

SUMMARY OF THE INVENTION

The present invention is concerned with the preparation of collagen compositions from invertebrate classes and species of marine animals constituting several hundreds of species of primitive marine animals, including species of jellyfish belonging to the class Scyphozoa, phylum Coelenterata. The present invention includes other classes of marine organisms and other species of invertebrates present in the marine environment where invertebrate type V collagen, the designation to be applied to collagens described by this present invention, possess similar physical and chemical characteristics. The present fibrous collagen products are unique and distinguished from previous collagen products formed from vertebrate animals species in that the marine invertebrate animals including jellyfish live and function in an environment different from that in which the vertebrate animal species live and function. For example, the marine jellyfish are found in salt-water environments hypertonic to vertebrate animals; are poikilothermal, i.e. have a body temperature that varies with the environmental temperature, and generally live and function at low temperatures compared to the body temperatures of most vertebrate species; live under variable pH conditions, but generally at pH values significantly less than "physiological" pH (pH 7.4) characteristic of vertebrate species; and lack significant tensile strength in their body structures. These attributes, i.e. pH, temperature, salt concentration, and tensile properties, represent important parameters used in the extraction and preparation of collagens from vertebrate species and thus, extraction and preparation of collagens from marine jellyfish would constitute a unique and novel process and the collagen preparation would have unique and novel properties even compared to type V collagen preparations from vertebrate species.

In the present invention, invertebrate marine animals including jellyfish of various genera, are subjected to mild mechanical disruption followed by mild acid solubilization of the disrupted tissue. Collagens are precipitated by salts with mild shearing and/or by continuous dialysis and are formed into aqueous, gelled, precipitated, and/or mat/sponge preparations. The fibrous collagen preparation(s), constitute primarily invertebrate type V telopeptide containing collagen, and are useful in a variety of medical, dental, nutritional applications, and/or as component(s) of cosmetics and other pharmacologicals depending on the purity of the collagen preparation and/or heterogeneity of jellyfish components allowed to remain in the preparations. The fibrous aggregates may be used directly for a variety of purposes or may be cross-linked to provide fibers having substantial structural integrity and macroscopic dimensions. Depending on the intended use of the fibrous materials, the fibers and/or other resident natural components may be treated in a variety of ways to prepare various articles of manufacture.

An object of the present invention is to provide substantially pure marine invertebrate type V telopeptide containing collagen.

A further object of the present invention is to provide a cosmetic composition containing marine invertebrate type V telopeptide containing collagen.

Another object of the present invention is to provide a cosmetic cream composition containing marine invertebrate type V telopeptide containing collagen.

An object of the present invention is to provide a cosmetic lotion composition containing marine invertebrate type V telopeptide containing collagen.

An additional object of the present invention is to provide a shampoo composition containing marine invertebrate type V telopeptide containing collagen.

An object of the present invention is to provide a hair conditioner composition containing marine invertebrate type V telopeptide containing collagen.

A further object of the present invention is to provide a makeup formulation containing marine invertebrate type V telopeptide containing collagen.

Another object of the present invention is to provide a colored cosmetic formulation containing marine invertebrate type V telopeptide containing collagen.

A further object of the present invention is to provide a cosmetic composition containing marine invertebrate type V telopeptide containing collagen in an amount of from 0.001 wt % to 30.000 wt %.

An object of the present invention is to provide a cosmetic composition containing marine invertebrate type V telopeptide containing collagen in an amount of from 0.1 wt % to 10.0 wt %.

An additional object of the present invention is to provide a cosmetic composition containing marine invertebrate type V telopeptide containing collagen in an amount of from 0.5 wt % to 5.0 wt %.

A further object of the present invention is to provide a process for preparing the present marine invertebrate type V telopeptide containing collagen by extracting, the collagen from a marine animal, in dilute acid; precipitating the extracted collagen, and washing the collagen precipitate.

An object of the present invention is to provide fibrillar marine invertebrate type V telopeptide containing collagen.

Another object of the present invention is to provide a cosmetic composition containing fibrillar marine invertebrate type V telopeptide containing collagen.

An additional object of the present invention is to provide marine invertebrate type V telopeptide containing collagen in the form of a gel.

DETAILED DESCRIPTION OF THE PREFERRED EMBODIMENTS

Definitions

In order to provide a clear and consistent understanding of the specification and claims, including the scope to be given such terms, the following definitions are provided.

Cosmetic composition. By the term "cosmetic composition" is intended for the purposes of the present invention any composition or agent for external application to human or animal skin, nails, or hair for the purpose of beautifying, coloring, conditioning, or protecting the body surface containing a cosmetically effective amount of marine invertebrate type V telopeptide containing collagen. A cosmetically effective amount of such collagen is that amount required to bring about the desired cosmetic effect, with from 0.001 wt % to 30.000 wt % being preferred, 0.1 wt % to 10.0 wt % more preferred, and 0.5 wt % to 5.0 wt % being most preferred. One of ordinary skill in the art to which the present invention pertains can readily determine what constitutes a "cosmetically effective amount" without undue experimentation. The present cosmetic composition can be in any form including for example: a gel, cream, lotion, makeup, colored cosmetic formulations, shampoo, hair conditioner, cleanser, toner, aftershave, fragrance, nail enamel, and nail treatment product.

Colored cosmetic formulation. By the term "colored cosmetic formulation" is intended for the purposes of the present invention those cosmetics containing pigment including for example eye shadow, lipsticks and glosses, lip and eye pencils, mascara, and blush.

Conditioning agent. By the term "conditioning agent" is intended any agent or composition which exerts a conditioning effect on the body including the skin, hair and/or nails upon external application and includes for example humectants; emollients; oils including for example mineral oil; proteins including the present collagen; and shine enhancers including for example dimethicone and cyclomethicone. The present conditioning agents maybe included in any of the present pharmacological and/or cosmetic compositions.

Telopeptide containing. By the term "telopeptide containing" is intended for the purposes of the present invention a marine invertebrate type V collagen composition where the composition includes collagen molecules where the nonhelical terminal portions of the native collagen molecule, the telopeptides which extend as random coils from the amino and carboxyl ends of the collagen molecule, are retained.

Atelopeptide containing. By the term "atelopeptide containing" is intended for the purposes of the present invention a marine invertebrate type V collagen composition where the composition includes collagen molecules where the nonhelical terminal portions of the native collagen molecule, the telopeptides, have been removed for example by enzymatic cleavage.

Fibrillar collagen. By the term "fibrillar collagen" is intended for the purposes of the present invention, a natural polymeric form of collagen which is essentially insoluble in its aqueous environment yet forms a viscous gel-like matrix.

Invertebrate marine animal. By the term "invertebrate marine animal" is intended for the purposes of the present invention, invertebrate animals present in a salt-water or fresh-water marine environment and include for example members of the phylum Coelenterata, members of the class Scyphozoa and the phylum Coelenterata including for example jellyfish.

Pharmacological compositions. By the term "pharmacological compositions" is intended for the purposes of the present invention any composition or agent applied externally to the skin, hair, or nails of the human or a animal body for therapeutic purposes containing a pharmacologically effective amount of the present marring invertebrate type V telopeptide containing collagen. A "pharmacologically effective amount" is that amount required to bring about the desired therapeutic effect, with 0.001 wt % to 30.000 wt % being preferred, 0.1 wt % to 10.0 wt % more preferred, and 0.5 wt % to 5.0 wt % being most preferred. One of ordinary skill in the art to which the present invention pertains can readily determine what constitutes a "pharmacologically effective amount" without undue experimentation. Examples of pharmaceutical agents or compositions in accordance with the invention include ointments, creams, lotions, gels, solutions, and shampoos. More specific examples include for example, acne treatment preparations including creams, soaps, cleansers, moisturizers, ointments and lotions; anti-aging preparations including creams, cleansers, moisturizers and lotions; anti-dandruff preparations including shampoos and conditioners; antibiotic preparations; sunburn preparations; anti-itch preparations; and anti-fungal preparations.

The present non-cross-linked or cross-linked fibrillar telopeptide containing collagen may be used directly as a gel. As a gel, the fibrillar collagen can be used as a vitreous body or as dispersions/solutions for the preparation of cosmetic and pharmacological compositions. The fibrillar collagen can be cast into various forms at varying collagen fiber density and cross-linked to form mat or sponge-like structures which may be used in a variety of applications such as delivery of pharmaceutical agents to hair or skin, as artificial nails, as prosthetics, theatrical devices, etc. Articles of matter produced using marine invertebrate type V telopeptide containing fibrillar collagen are different from similar articles of matter produced using collagen preparations obtained from vertebrate species.

A method is provided for preparation of commercially useful amounts of essentially type V collagen from marine jellyfish which may be formed into a variety of formulations and/or products. The collagen is most conveniently prepared from the whole organism, but the hemispherical bell-shaped transparent umbrella may be separated from the numerous fine marginal tentacles and reproductive and/or digestive structures present in the umbrella may be removed and the partial umbrella used in the production of various collagen preparations. Depending on the intended use of the derived fibrous materials, the native collagen may be freed of extraneous matter such as lipids, saccharides, and noncollagenous proteins so as to leave an essentially purified preparation of type V collagen. Another approach includes using fibrous materials in the preparation of a "natural" cosmetic such as a hair or skin cleaning/conditioning preparation and in this application of the present invention, the native collagen may be less extensively purified such that the natural material components of the jellyfish are retained in the product(s).

The nonhelical terminal portions of the native collagen molecule, the telopeptides, extend as random coils from the amino and carboxyl ends of the molecules and may be retained or enzymatically removed in preparation of the final product(s). The telopeptides serve a number of functions in the formation of the native collagen fiber. The telopeptides serve as the primary sites for cross-linking intramolecularly (between the three constituent polypeptide chains in the native collagen molecule) and intermolecularly (between two or more native collagen molecules).

In a preferred embodiment of the present invention, native essentially type V marine invertebrate telopeptide containing collagen is produced essentially free of noncollagenous proteins and other substances naturally present in marine jellyfish. This collagen is soluble in dilute aqueous acid, e.g. 0.01 M acetic acid, and 0.001 N HCl, and any insoluble collagen, if present, may be removed by filtration, centrifugation, or other means.

In another preferred embodiment of the present invention, native essentially type V marine invertebrate telopeptide containing collagen is produced which retains appropriate noncollagenous proteins and/or polysaccharides naturally present in marine jellyfish. This collagen preparation is soluble in dilute aqueous acids and nonsoluble components and or tissue structures may be removed by filtration, centrifugation, or other means.

Once the collagen solution is obtained, it may be employed for preparing fibrous aqueous solutions, fibrous aqueous gels, and dispersions/solutions of these products in surfactant solutions containing other ingredients suitable for the preparation of hair and skin treatments, and cosmetic and pharmacological compositions. The procedure for preparing the fibrous preparations involves a slow precipitation of the collagen from solution while subjecting the aqueous medium to mild shear (stirring). The conditions under which the precipitation of the collagen is achieved can vary. The temperatures employed are preferably in the range of from 0° C. to 42° C., more preferably from 10° C. to 30° C., and most preferably from 15° C. to 25° C. The pH is generally in the range of about 3 to 9, preferably in the range of 5 to 8, and more preferably between 6 and 7.5. A wide variety of salts may be used, usually alkali metal salts, both neutral and alkaline, more particularly sodium and potassium, with mono and polyvalent cation salts, particularly halides, e.g. chloride. The concentration of the salt may vary widely with the other conditions employed, e.g. temperature, and protein concentration, as well as the particular salt employed. Suitable concentrations are preferably in the range of from about 0.05 M to 4.0 M, more preferably from 1.0 M to 3.8 M, and most preferably between 2.5 M and 3.5 M. Suitable concentrations of polyvalent salts are in the range of from about 0.5 M to 4.0 M, more preferably from 1.0 M to 4.0 M and most preferred concentrations ranging from 2.5 M to 4.0 M. The concentration of collagen in the solutions being precipitated may range between 0.01 mg/ml and 10 mg/ml, preferably in the range of from 0.1 mg/ml to 5 mg/ml, and most preferably from 0.5 mg/ml and 4 mg/ml. Precipitation time varies from about 10 minutes to 5 hours, usually about 30 minutes to 2 hours, and preferably about 1 hour to 1.5 hours.

Various techniques may be used to obtain the desired rate of precipitation of collagen while applying the mild shearing. One technique is heat gelation, wherein a constant or slowly increasing temperature is employed to bring about precipitation of collagen in the presence of salt. Generally, the temperature range is from about 4° C. to 45° C., the temperature being slowly raised from about 4° C. to 10° C. to a temperature of about 20° C. to 37° C. Salt concentrations generally vary from about 1.0 M to 4.0 M. Alkali metal halides, e.g. sodium chloride, are preferably employed. The pH is generally from 4.0 to 8.0, preferably 5.0 to 6.0. Particularly preferred conditions are nonphysiological conditions for the jellyfish, namely 3.5 M NaCl, pH 5.0, with a final temperature of about 35° C.

A second technique is to provide a slow increase in ionic strength, pH, and temperature with the collagen in solution. This can be achieved by employing dialysis with a monovalent or polyvalent salt dialysate, thereby slowly raising the salt concentration (or ionic strength) while the acid in the collagen solution diffuses from the collagen solution into the dialysate. The change in pH can be either continual or incremental, typically by employing alkali salts in the dialysate. Usually the dialysate has a salt concentration of 1.0 M to 4.0 M, more usually to 2.5 M to 3.8 M, particularly of disodium phosphate. The final pH of the medium is generally 3.0 to 8.5, more usually 4.0 to 6.5, and preferably 5.0 to 5.5.

Another procedure is that of continuous dialysis at moderately reduced to low temperatures while changing the dialysate from a dilute mildly acidic solution to (generally a mild mono or dicarboxylic organic acid or dilute mineral acid such as HCl) to a mildly basic salt solution, while increasing the ionic strength or salt concentration by using a dialysate of increasing salt concentration. With increasing ionic strength or salt concentration, the temperature of the solution may also be increased, until a fibrous mass of obtained. The fibrous mass is freed of any nonfibrous materials and may be treated in a variety of ways depending on the intended use.

Another use of the present collagen preparations include the addition of the preparation into solutions of surfactants, detergents, soaps, and similar formulations for use with treatment of hair and skin as a cosmetic, a cosmetic ingredient, and/or pharmacological agent. The term "cosmetic ingredient" is the same as "cosmetic composition" and means a composition applied externally to skin, nails, or hair of the human or animal body, for purposes of beautifying coloring, conditioning, cleansing, or protecting the bodily surface. Examples of cosmetic ingredients or cosmetic compositions in accordance with the invention include lotions, creams, moisturizers, gels, sun screens, makeup, cleansers, soaps, shampoos, hair conditioners, skin firming compositions, protein concentrates, after shaves, colored cosmetics including for example eye shadows and blushes, nail enamels, and so forth. Vertibrate animal collagen is known to have moisturizing and film forming properties, and is a popular additive to treatment cosmetics. The term "pharmacological agent" is the same as "pharmacological composition" and means an agent or composition applied externally to the skin, hair, or nails of the human or an animal body for therapeutic purposes. Examples of pharmaceutical agents or compositions in accordance with the invention include ointments, creams, lotions, gels, soaps, solutions, and shampoos.

Animal collagen protein is the main component of connective tissues and animal keratin is the main component of hair and fingernails. Collagen is responsible for most of skin structure. In the course of aging the polypeptide chains of collagen polymerize. The result is "cross-linking", which causes wrinkling of the skin as well as reduction in skin elasticity. Keratin is responsible for the most of hair structure. In the course of hair growth, the keratins dry out and exhibit cracks in surface structure of hair. Collagens are natural film forming agents and aid in prevention of drying. The present collagen preparation can be added to a typical shampoo composition by weight, an example of which is set forth below:

| Trade Name | CTFA Name | Weight Percent |
|---|---|---|
| Sulfotex UBL 100 acid | Dedecybenzene Sulfonic Acid | 3.0 |
| Triethanolamine | Triethanolamine | 1.7 |
| DI water | | 50 |

-continued

| Trade Name | CTFA Name | Weight Percent |
|---|---|---|
| Invertebrate Type V Collagen | | 0.5 |
| Panthenol | Panthenol | 0.24 |
| Sulfotex LMSE | Sodium Laureth Sulfate | 15.0 |
| Sulfotex WA | Sodium Lauryl Sulfate | 10.0 |
| Germaben II | Propylene Glycol | 56.0 |
| | Diazolidinyl Urea | 30.0 |
| | Methyl Paraben | 11.0 |
| | Propyl Paraben | 3.0 |
| Ninol LL-50 | Lauramide DEA | 7.0 |
| DC 929 | Amodimethyl (and) Nonoxynol-10 and Tallowdimonium Chloride | 1.0 |
| D&C Yellow #5 Solution | | 0.04 |
| Clindrol SEG | Glycol Stearate (optional) | 2.0 |

In addition, the present material can be added to various formulations of skin care products generally described as lotions for application to human facial or body skin. These lotions generally contain from about 20–80% oil and 10–80% water in an emulsion form. In addition, the moisturizing lotion may contain humectants, emollients, surfactants, fragrances, preservatives, and so forth. About 5–10% humectant, about 5–20% emollient, and about 0.5–10% surfactant are suggested. Marine invertebrate Type V telopeptide containing collagen (at about 0.01 to 1.00 wt %) and hydrolyzed collagen (at about 0 1 to 2.0 wt %) products may be incorporated into moisturizing creams. Creams generally contain from about 20–70% water and about 30–70% oil. In addition, creams may contain a variety of humectants, emollients, surfactants, preservatives, and fragrances. About 5–10% humectant, about 5–20% emollient, and about 0.5–10% surfactant are suggested.

Marine invertebrate Type V telopeptide containing collagens (incorporated at about 0.01 to 5.0 wt %) and hydrolyzed collagen (incorporated at about 0.1 to 10.0 wt %) products may be incorporated into treatment makeups. Generally, makeup formulations comprising 5–70% oil, 10–95% water, and about 5–40% pigment, are suitable. In addition, the makeup as well as any of the present cosmetic or pharmacologic compositions may contain other components known and readily selected by those of ordinary skill in the art to which the present invention pertains. For makeup formulations such components may include for example surfactants, preservatives, silicone, humectants, emollients, and fragrances. Generally 0.5–10% surfactant, 0.1–30% silicone, 5–10% humectant, 0.1–30% emollient, and 0.1–5% preservative are included.

Marine invertebrate Type V telopeptide containing collagens (about 0.2 to 2.0 wt %) and hydrolyzed collagen (about 0.01 to 5.00 wt %) products may be incorporated into colored cosmetics such as eye shadow or blush. For example, a suitable eye shadow comprises 5–40% pigment, 1–50% oil, and 1–20% waxes. Additionally, the composition may contain one or more of 10–60% water, 0.5–30% surfactant, 1–10% humectants, 0.1–5% preservative, and 0.1–20% silicone.

Invertebrate Type V collagens (about 0.01 to 2.00 wt %) and hydrolyzed collagen (about 0.01 to 5.00 wt %) products may suitable for incorporation into shampoos and hair conditioners. Suitable shampoo formulations include 1–40% surfactant and 10–90% water Suitable hair condition formulations include 30–95% water, 0.5–30% conditioning ingredients including for example, emollients, proteins, and shine enhancers, and 1–40% surfactant. Hair conditioners and shampoos may also contain thickeners and silicone. About 0.05–5% silicone is suggested in shampoos and hair conditioners.

The invention includes cosmetic and pharmaceutical compositions containing a cosmetically or pharmaceutically effective amount of invertebrate type V telopeptide containing collagen protein. A cosmetically and/or pharmacologically effective amount of collagen protein in accordance with the invention is that amount required to bring about the desired cosmetic and/or therapeutic effect. Such amount can readily selected by one of ordinary skill in the art to which the present invention pertains based on the particular formulation and the desired effect, without undue experimentation. Preferably, about 0.001–30 wt %, more preferably 0.1–10 wt %, and most preferably 0.5–5 wt % is employed.

In describing the present invention, three stages will be considered. The first stage is the purification of native collagen and its transformation into collagen in solution. The second stage is the transformation of the collagen in solution into native fibrous polymers. The third stage is the use of the native collagen, collagen in solution, and fibrous polymers, for the fabrication of various articles or the formation of composites.

Suitable collagen sources include a wide variety of marine animals such as those of the phylum Coelenterata. Collagen dispersions or solutions obtained from the mantle, tentacles, and whole organism provide similar collagen dispersions or solutions. First the reproductive and digestive tissue structures and tentacles, are removed from the organism. The mantle portion of the jellyfish provides the most uniform materials for production of collagen dispersions or solutions with the least amount of noncollagenous protein material(s). For purposes of this invention, collagen dispersion or solutions are defined as aqueous compositions where the collagen does not settle away from the aqueous composition under normal conditions of preparation and storage.

To enhance the ease of purification and facilitate dispersion/solubilization of collagens, the material is subjected to various mechanical treatments such as dissection, grinding, high speed shearing, and the like. Depending on the particular treatment, the tissue may be wet or dry, frozen or cooled, high speed shearing is preferably carried out with frozen or cooled wet tissue, and grinding is preferably carried out with dry cooled tissue.

Coarsely divided tissues are swollen in aqueous acidic solutions under nondenaturing conditions. Further dispersion is achieved using high speed shearing in short bursts. Preferably dilute acid solutions at low temperatures are employed to minimize denaturation. Suitable acids include acetic, citric, malonic, or lactic acids, or other carboxylic acids having pK values from about 2 to 5 at room temperature. Dilute mineral acids such as HCl may also be used provided the pH of the dilute acid solution is approximately 2 to 5. Concentrations of the organic acid in the dispersion medium typically range from about 0.01 M to 1.0 M and the temperature may vary from 4° C. to about 25° C. Preferably, 0.5 M acetic or citric acid solubilization for 2–3 days yields a collagen dispersion which may be filtered through cheesecloth. The acid soluble extract may be dialyzed against sodium phosphate buffer and the formed precipitate redissolved in 0.5 M acetic or citric acid. Solid NaCl may be slowly added to the acid solubilized preparation to a final concentration of about 3.5 M to effect secondary precipitation. Precipitated collagen dispersion may be redissolved in dilute acid and freeze-dried.

Preparation of atelopeptide collagen dispersion maybe accomplished by solubilizing collagen or dissolving the freeze-dried collagen preparation in dilute acid and digesting the materials with 4–10%, weight per weight, pepsin, ficin, collagenase, trypsin and pronase at 4° C. After 24 hours, the digest may be dialyzed against sodium phosphate and precipitated by addition of solid NaCl and/or the dialysate may be concentrated by freeze-drying. The formed precipitate may be redissolved in dilute acid and freeze-dried.

In the present invention, mantle from jellyfish is a preferable source of collagen, where the collagen-containing material is separated from adjacent tissues by dissection, soaked in dilute acid at room temperature and ground using short bursts of high speed shear (for example, using a blender). This technique provides a homogeneous dispersion of jellyfish which is readily available to subsequent treatment, so as to provide an efficient means for achieving collagen in solution.

The dispersion which is obtained by treatment with acid is a viscous dispersion containing native (telopeptide containing collagen) fibrillary collagen and a small amount of native collagen in solution.

The viscous product, i.e. dispersed swollen collagen, is marine invertebrate type V telopeptide containing collagen of the composition alpha1alpha2alpha3. Enzymatic treatment may be used at this point to remove telopeptides producing atelopeptide fibrillar collagen while leaving the major portion of the molecule intact. Illustrative enzymes include for example, pepsin, ficin, collagenase, trypsin, and pronase.

Depending on the particular enzyme employed, conditions for enzymatic cleavage of the telopeptides vary. With pepsin an acidic solution is employed, generally at a pH of about 2 to 4. The concentration of the enzyme varies from about 0.001 to 10 wt % based on the weight of collagen present. The collagen concentration generally varies from 0.5 g/l to 10 g/l, more usually from about 1 g/l to 5 g/l.

Preferably, the acidity is provided by an organic acid such as a carboxylic acid in a concentration of about 0.01 M to 1.0 M. If necessary, the pH can be adjusted by the addition of a mineral acid, e.g. hydrochloric.

The solution of soluble fibrillar collagen is then treated to separate the soluble fibrillar collagen from soluble noncollagenous materials. Primarily, the treatment involves separations, precipitations, and dialysis against various solutions of different ionic strength known to those of ordinary skill in the art, and readily selected and employed by those of ordinary skill in the art to which the present invention pertains without undue experimentation. Moderate temperatures are employed, normally between 0° C. and 20° C., and salt solutions of varying ionic strength and salt concentration, generally from about 0.01 M to 4.0 M. depending on the particular salt.

Neutral salt solutions, e.g. NaCl, of about 0.5 M to 4.0 M may be employed as a dialysate in a free-flow dialysis at a pH of at least 5 and not greater than about 9. Non-soluble contaminants which have been precipitated during preparation of soluble fibrillar collagen are filtered off to yield a filtrate which contains atelopeptide containing collagen in solution.

The collagen in dispersion/solution (telopeptide and/or atelopeptide) is precipitated as a part of a purification scheme, for example by adding a neutral salt to the solution to a concentration of about 1.0 M to 4.0 M, preferably 3.5 M. Various alkali metal halides, e.g. NaCl, may be used. The resulting precipitate is isolated, for example by centrifugation. Further treatment includes exchanging with a dilute carboxylic acid, e.g. acetic acid (0.05 M to 0.5 M) in the presence of aqueous NaCl (0.001 to 0.1 weight percent) with precipitation by addition of NaCl (1 to 4 M) and resolubilization to insure the purity of the collagen. Specifically, the procedure may involve an initial precipitation by use of a neutral salt (at least 10 to 30 wt %), isolation of the precipitate, redissolving in dilute acid, e.g. a carboxylic acid of about 0.05 M to 1.0 M, filtration, reprecipitation of the collagen with about 2 to 10 wt % aqueous salt solution, isolation, redissolution with a dilute carboxylic acid, with repetition of the purification process until the desired degree of purity. The collagen is then resuspended in dilute acid solution, generally a carboxylic acid such as acetic or citric acid at a concentration of about 0.01 M to 0.5 M. Activated charcoal can be added in particle tight containers or the collagen can be dialyzed to remove low molecular weight solutes which might present undesirable odors or fragrances.

Precipitation of the collagen can be achieved in a variety of ways, including for example, the addition of neutral salt, and decrease in pH in the presence of neutral salt. Preferably, mild conditions are employed to prevent denaturation and disruption of the natural fibrillar character of collagen. The collagen dispersion may then be concentrated, for example by dialysis, to a concentration of about 1 mg/ml to 20 mg/ml. The clear solution of collagen is relatively free of higher aggregates, is viscous, and consists essentially of marine invertebrate type V fibrillar collagen.

In the preparation of cosmetic or pharmaceutical products using the present invention, marine invertebrate type V collagen can be used in effective amounts of about 0.001 to 30 wt % of the collagen protein preparation, with 0.01 to 10 wt % preferred, and 0.5 to 5 wt % most preferred. The collagen proteins may be incorporated into suitable cosmetic or pharmaceutical vehicles such as lotions, creams, ointments, gels, shampoos, conditioners, or solutions. Suitable ointments are hydrophilic ointments (USP) or petrolatum and cosmetically effective amounts of collagen protein are incorporated into the ointment for topical application to skin or hair. Suitable lotions and creams are as mentioned previously for cosmetic compositions. Solutions are made by mixing solutions of collagen protein in deionized water for application to human or animal skin and hair. Gels are made by mixing 1–90% water with a suitable polymer.

Suitable humectants for use in the cosmetic compositions of the present invention include for example glycerin, propylene glycol, butylene glycol, urea, sorbitol, sodium PCA, gelatin, polyethylene glycols, sodium lactate, and hyaluronic acid.

Suitable emollients include for example glyceryl stearate, cetyl alcohol, stearyl alcohol, isopropyl stearate, stearyl alcohol, stearyl stearate, isopropyl stearate, stearic acid, isobutyl palmitate, isocetyl stearate, oleyl alcohol, sebacates, myristates, palmitates, squalenes, glyceryl monooleate, oleic acids, lanolin, acetylated lanolin alcohols, petrolatum, mineral oils, palmitic acids, and isostearyl neopentanoate.

A variety of surfactants can be used in the compositions of the invention including amphoteric, anionic, cationic, or nonionic surfactants. Suitable amphoteric surfactants include imidazolines, betaines, and amino acid salts. Suitable anionic surfactants include for example fatty acid soaps, salts of higher alkyl sulfates, n-acyl sarcosinates, salt or phosphates, sulfosuccinate salts, alkyl benzene sulfonates, salts of N-acyl glutamate, and polyoxyethylene alkyl ether carboxylic acids. Cationic surfactants include for example alkyl trimethyl ammonium salts, alkyl pyridinium salts, alkyl quaternary ammonium salts, and polyamine fatty acid derivatives. Nonionic surfactants include for example lipophilics such as sorbitan fatty acid esters, glycerol fatty acids, propylene glycol fatty acid esters; hydrophilics including for example polyoxyethylene sorbitan fatty acid esters, polyoxyethylene glycerol fatty acid esters, polyoxyethylene fatty acid esters, polyoxyethylene alkyl ethers, pluronics, polyoxyethylene alkyl phenyl ethers, and polyoxyethylene propylene glycol fatty acid esters.

Suitable pigments include for example organic and inorganic pigments such as talc, mica, titanium dioxide, titanated mica, iron oxides, ultramarines, chromium oxides, carmine, D&C, and FD&C colors and lakes, ferric and ferrous oxides.

Suitable waxes include for example beeswax, carnauba, ceresin, microcrystalline, lanolin, candelilla, cetyl alcohol, cocoa butter, petrolatum, hydrogenated caster oil, spermaceti, bran wax, capok wax, and bayberry.

The present invention is directed to a method of moisturizing and forming a film on human and animal skin, nails, or hair by applying to the surface and effective amount of invertebrate type V telopeptide containing collagen protein. An effective amount of collagen protein is about 0.001–30 wt %. The collagen protein may be applied directly to the surface in a solution form, or it may be incorporated into cosmetic or pharmaceutical compositions mentioned herein. The collagen protein or protein containing composition may be applied to the surface once or twice a day or as necessary. For example, if the collagen protein is incorporated into a facial moisturizer, usually one to two applications of moisturizer per day will provide a beneficial effect. If the collagen proteins are incorporated into shampoos or hair conditioners, usually application once a day or every other day will be sufficient to provide a beneficial effect. When collagen proteins are incorporated into makeups, blushes, or eye shadows, they provide a treatment effect to the skin when applied once a day or whenever makeup is worn. If incorporated into nail treatment products or nail enamels, consistent usage in a nail care regimen (i.e. once or twice a week) will provide beneficial results.

The invention will be further described in connection with the following examples which are set forth for the purposes of illustration only.

EXAMPLE 1

Preparation of Marine Invertebrate Type V Telopeptide Collagen Gel:

Cannon-ball jellyfish were dissected to separate the mantle from the tentacles and the reproductive and digestive organ was dissected from the mantle. The mantle was then cut into small pieces and placed into dilute (0.5 M) citric acid such that 10 mantles of average sized jellyfish (8–12 inches in diameter) were placed into 4 liters of citric acid solution. The container was covered to restrict evaporation and refrigerated at between 4° C. and 10° C. for three (3) days. The viscous collagen solution was filtered through 4 layers of cheese-cloth and the viscous materials precipitated by the addition of solid sodium chloride to a final concentration of 3.5 M. The sodium chloride was added in small increments and the precipitated materials removed as formed by the salt precipitation. Essentially all of the collagen was thus precipitated by the addition of sodium chloride and transferred to a separate container. The precipitated collagen was then gently and quickly washed with distilled water to remove associated salt crystals and then 1 liter of 0.5 M citric acid solution was added to resolubilize the precipitated collagen. This aqueous solution of invertebrate type V collagen was stored in a tight container, to prevent evaporation, under refrigeration until used. By sampling aliquots of this collagen preparation it was determined that the collagen content was 2.5% by weight. A particle tight container of activated charcoal was added to the collagen preparation during storage to reduce odors.

EXAMPLE 2
Preparation of Marine Invertebrate Type V Telopeptide Collagen Solution:

In this example, cannon-ball jellyfish were dissected to separate the mantle from the tentacles and the reproductive and digestive organ was dissected from the mantle. The tentacles were then cut into small pieces and placed into dilute (0.5 M) citric acid such that tentacles from 10 average sized jellyfish (8–12 inches in diameter) were placed into 2 liters of citric acid solution. The container was covered to restrict evaporation and refrigerated at between 4° C. and 10° C. for three (3) days. The viscous collagen solution was filtered through 4 layers of cheese-cloth and the viscous materials precipitated by the addition of solid sodium chloride to a final concentration of 3.5 M. The sodium chloride was added in small increments and the precipitated materials removed as formed by the salt precipitation. Essentially all of the collagen was thus precipitated by the addition of sodium chloride and transferred to a separate container. The precipitated collagen was then gently and quickly washed with distilled water to remove associated salt crystals and then 1 liter of 0.5 M citric acid solution was added to resolubilize the precipitated collagen. This aqueous solution of invertebrate type V collagen was stored in a tight container, to prevent evaporation, under refrigeration until used. By sampling aliquots of this collagen preparation it was determined that the collagen content was 1.8% by weight.

EXAMPLE 3
Preparation of Marine Invertebrate Type V Telopeptide Collagen Gelatin:

In this example, cannon-ball jellyfish were dissected to separate the mantle from the tentacles and the reproductive and digestive organ was dissected from the mantle. The mantle was then cut into small pieces and placed into dilute (0.5 M) citric acid such that 10 mantles of average sized jellyfish (8–12 inches in diameter) were placed into 4 liters of citric acid solution. The container was covered to restrict evaporation and heated to a temperature of 65° C. for 15 minutes (the solution appears to clear after approximately 10 minutes, however heating was continued until the solution temperature reached 70° C. at which time the collagen preparation was placed refrigerated at between 4° C. and 10° C. for three (3) days. The viscous gelatin solution was filtered through 4 layers of cheese-cloth and the viscous materials or aqueous solution of invertebrate type V gelatin was stored in a tight container, to prevent evaporation, under refrigeration until used. By sampling aliquots of this gelatin preparation it was determined that the collagen content was 2.8% by weight. A particle tight container of activated charcoal was added to the gelatin preparation during storage to reduce odors.

EXAMPLE 4
Preparation of Marine Invertebrate Type V Telopeptide Collagen Solution:

In this example, cannon-ball jellyfish were dissected to separate the mantle from the tentacles and the reproductive and digestive organ was dissected from the mantle. The mantle and tentacles were then cut into small pieces and placed into dilute (1.0 M) acetic acid such that 10 mantles and associated tentacles of average sized jellyfish (8–12 inches in diameter) were placed into 2 liters of acetic acid solution. The container was covered to restrict evaporation and refrigerated at between 4° C. and 10° C. for three (3) days. The viscous collagen solution was filtered through 4 layers of cheese-cloth and the viscous materials precipitated by the addition of solid sodium chloride to a final concentration of 3.5 M. The sodium chloride was added in small increments and the precipitated materials removed as formed by the salt precipitation. Essentially all of the collagen was thus precipitated by the addition of sodium chloride and transferred to a separate container. The precipitated collagen was then gently and quickly washed with distilled water to remove associated salt crystals and then 1 liter of 0.5 M citric acid solution was added to resolubilize the precipitated collagen. This aqueous solution of invertebrate type V telopeptide containing collagen was stored in a tight container, to prevent evaporation, under refrigeration until used. By sampling aliquots of this collagen preparation it was determined that the collagen content was 3.2% by weight. A particle tight container of activated charcoal was added to the collagen preparation during storage to reduce odors.

EXAMPLE 5
Preparation of Marine Invertebrate Type V Telopeptide Collagen-Freeze Dried:

In this example, cannon-ball jellyfish were dissected to separate the mantle from the tentacles and the reproductive and digestive organ was dissected from the mantle. The mantle and tentacles were then cut into small pieces and placed into dilute (1.0 M) acetic acid such that 10 mantles and associated tentacles of average sized jellyfish (8–12 inches in diameter) were placed into 2 liters of acetic acid solution. The container was covered to restrict evaporation and refrigerated at between 4° C. and 10° C. for three (3) days. The viscous collagen solution was filtered through 4 layers of cheese-cloth and the viscous materials precipitated by the addition of solid sodium chloride to a final concentration of 3.5 M. The sodium chloride was added in small increments and the precipitated materials removed as formed by the salt precipitation. Essentially all of the collagen was thus precipitated by the addition of sodium chloride and transferred to a separate container. The precipitated collagen was then gently and quickly washed with distilled water to remove associated salt crystals and then 1 liter of 0.5 M citric acid solution was added to resolubilize the precipitated collagen. This organic acid dispersion/solution of invertebrate type V collagen was then placed into dialysis bags and exhaustively dialyzed against deionized water at 0° C. (against crushed ice made with deionized water). This aqueous solution of invertebrate type V collagen was stored in a tight container, to prevent evaporation, under refrigeration until freeze-dried. By sampling aliquots of this collagen preparation it was determined that the collagen content was 3.2% by weight. A particle tight container of activated charcoal was added to the collagen preparation during storage to reduce odors. This deionized water dispersion of invertebrate type V collagen was carefully frozen in a freeze-drying vessel as to maximize the surface area to volume ratio, and freeze-dried. The freeze-dried collagen preparation was sealed under vacuum and stored at room temperature (for prolonged storage it is also possible to store this freeze-dried materials in a freezer at minus 20° C.). Prior to use in formulation of compositions containing this materials, the collagen was sheared in a waring blender to achieve a fine powder and then reconstituted in 0.25 M citric acid.

EXAMPLE 6

A collagen/gelatin containing oil in water moisturizing lotion was made as follows.

| Additive | w/w % |
| --- | --- |
| Glyceryl stearate | 3.5 |
| PPG-10 lanolin ether | 0.5 |
| Mineral oil | 6.0 |
| Lanolin alcohol | 0.8 |
| Oleic acid | 2.8 |
| Isocety stearate | 10.0 |
| Triethanolamine | 1.3 |
| Carbomer 941 | 0.1 |
| Glycerin | 9.0 |
| Preservative | 0.4 |
| Collagen solution | 5.0 |
| Water | qs 100.0 |

Marine invertebrate type V telopeptide containing collagen was used, preferably made according to example 1 or 2.

EXAMPLE 7

An oil in water moisturizing cream was made as follows:

| Additive | w/w % |
| --- | --- |
| Glyceryl stearate | 5.0 |
| Cetyl alcohol | 2.0 |
| Stearyl alcohol | 2.0 |
| Isopropyl stearate | 5.0 |
| Mineral oil | 13 |
| Polysorbate 60 | 1.0 |
| Glycerol | 9.0 |
| Zanthan gum | 0.3 |
| Preservative | 0.5 |
| Collagen solution | 5.0 |
| Hydrolyzed collagen solution | 5.0 |
| Water | qs 100.0 |

Marine invertebrate type V telopeptide containing collagen was used.

EXAMPLE 8

An oil/water cream makeup was made as follows:

| Additive | w/w % |
| --- | --- |
| Octyldodecy stearyl stearate | 4.0 |
| Isocetylstearate | 1.5 |
| Glyceryl stearate | 5.5 |
| Isotearic acid | 2.0 |
| Ceteth 10 | 1.0 |
| Cyclomethicone | 12.0 |
| Stearyl alcohol | 1.2 |
| Nonionic surfactant | 1.0 |
| Binders and Thickeners | 1.8 |
| Titanium dioxide | 8.0 |
| Iron oxide | 1.0 |
| Propylene glycol | 2.5 |
| Triethanolamine | 1.5 |
| Preservatives | 0.6 |
| Collagen Gelatin solution | 1.5 |
| Water | qs 100.0 |

Marine invertebrate type V telopeptide containing collagen was used, made according to any one of examples 1–5, more preferably made according to example 3, 4, or 5.

EXAMPLE 9

A protein shampoo was made as follows:

| Additive | w/w % |
| --- | --- |
| Ammonium lauryl sulfate | 9.0 |
| Sodium dodecyl sulfate | 1.0 |
| Cocamide diethanolamine | 4.0 |
| Cocamidopropyl betaine | 4.0 |
| Ammonium chloride | 0.8 |
| Collagen solution | 2.0 |
| Water | qs 100.0 |

Marine invertebrate type V telopeptide containing collagen was used, made according to any one of examples 1–6.

EXAMPLE 10

A creme rinse hair-conditioner was made as follows:

| Additive | w/w % |
| --- | --- |
| Stearalkonim chloride | 2.0 |
| Cetyl alcohol | 1.0 |
| Stearyl alcohol | 0.5 |
| Stearic acid | 0.5 |
| Ceteareth 20 | 2.0 |
| Xanthan gum | 0.5 |
| Dimethicone | 0.2 |
| Collagen Gelatin solution | 0.2 |
| Water | qs 100.0 |

Marine invertebrate type V telopeptide containing collagen was used, made according to any one of examples 1–6.

EXAMPLE 11

Preparation of a Natural Collagen Dispersion:

Cannon-ball jellyfish were gently homogenized using a mechanical grinder similar to that used to grind hamburger meat. The group materials were collected into suitable containers (5 gallon plastic pails with locking lids are suitable as are 55 gallon tanks) and citric acid was added in dry powder form to a final concentration of 0.5 M with constant stirring to dissolve and disperse the citric acid. The container was closed and stored under refrigeration (4–10C) for a minimum of 2 weeks. After two weeks, the containers were opened and the materials stirred using an electrically driven stirring device (an appropriate stirring device is one such as used to stir paint) to further homogenize the now viscous collagen preparation. The viscous collagen preparation was then filtered through fine screen wire to remove residual fragments of reproductive organs, and non-dispersed collagen/protein materials. The viscous clarified materials were returned to storage containers and stored under refrigeration until use. The produced natural collagen preparation is useful in formulations of a variety of products both hydrolyzed and non-hydrolyzed The natural collagen retains the natural salt and small molecular weight materials present in the source materials and can be preserved using chemical preservatives for storage without refrigeration, it can be diluted to provide less viscous collagen preparations, it can be heated to produce gelatin preparations. More specifically, this natural material is a base material which can be used with additional processing to produce the materials described in all other Examples.

Although the present invention has been described with reference to the presently preferred embodiments, the skilled artisan will appreciate the various modifications, substitutions, omissions, and changes may be made without departing from the spirit of the invention. Accordingly, it is intended that the scope of the present invention be limited only be the scope of the following claims, including equivalents thereof. All references cited herein are hereby incorporated by reference in their entirety.

What is claimed:

1. A cosmetic composition, comprising
   (a) marine invertebrate type V telopeptide collagen and
   (b) at least one of an emollient, a wax, or from about 1.3 wt % to 30 wt % surfactant.

2. The cosmetic composition of claim 1, further comprising marine invertebrate type V atelopeptide collagen.

3. The cosmetic composition of claim 1, wherein the marine invertebrate type V telopeptide collagen is crosslinked.

4. The cosmetic composition of claim 1, wherein the marine invertebrate type V telopeptide collagen comprises between 0.25 wt % and 95.0 wt % collagen protein.

5. The cosmetic composition of claim 1, wherein said collagen is fibrillar.

6. The cosmetic composition of claim 1, wherein said cosmetic composition is a cream, a lotion, a gel, a makeup, an eye shadow, a blush, a shampoo, a hair conditioner, a cleanser, a toner, an aftershave, a fragrance, a nail enamel, or a nail treatment.

7. The cosmetic composition of anyone of claims 1, 5, or 6 wherein said marine invertebrate collagen is present in said cosmetic composition in an amount of from about 0.001 wt % to 30.000 wt %.

8. The cosmetic composition of claim 7, wherein said marine invertebrate collagen is present in said cosmetic composition in art amount of from 0.100 wt % to 10.000 wt %.

9. The cosmetic composition of claim 8, wherein said marine invertebrate collagen is present in said cosmetic composition in an amount of from 0.200 wt % to 5.000 wt %.

10. The cosmetic composition of anyone of claims 1, 5, or 6 wherein said marine invertebrate collagen is isolated from one or more species belonging to the class Scyphozoa in the Coelenterata.

11. The cosmetic composition of claim 10, wherein said collagen is isolated from one or more species of jellyfish.

12. The cosmetic composition of claim 11, wherein said marine invertebrate collagen is present in said cosmetic composition in an amount of from about 0.001 wt % to 30.000 %.

13. The cosmetic composition of claim 12, wherein said marine invertebrate collagen is present in said cosmetic composition in an amount of from 0.100 wt % to 10.000 wt %.

14. The cosmetic composition of claim 13, wherein said marine invertebrate collagen is present in said cosmetic composition in an amount of from 0.200 wt % to 5.000 wt %.

15. An additive suitable for incorporation into at least one of a cosmetic composition or a pharmaceutical composition, wherein the additive consists essentially of a fibrillar marine invertebrate type V telopeptide collagen.

16. The additive of claim 15, wherein the fibrillar marine invertebrate type V telopeptide collagen is in the form of a gel or a solution.

17. A cosmetic cream, comprising:
    20.0 wt % to 70.0 wt % water; 30.0 wt % to 70.0 wt % oil; and 0.001 wt % to 30.000 wt % marine invertebrate type V telopeptide collagen.

18. The cosmetic cream of claim 17, further comprising marine invertebrate type V atelopeptide collagen.

19. A cosmetic lotion, comprising:
    10.0 wt % to 80.0 wt % water; 20.0 wt % to 80.0 wt % oil; and 0.001 wt % to 30.000 wt % marine invertebrate type V telopeptide collagen.

20. The cosmetic lotion of claim 19, further comprising marine invertebrate type V atelopeptide collagen.

21. A shampoo composition, comprising:
    10.0 wt % to 90.0 wt % water; 1.0 wt % to 40.0 wt % surfactant; and 0.001 wt % to 30.00 wt % marine invertebrate type V telopeptide collagen.

22. The shampoo composition of claim 21, further comprising marine invertebrate type V atelopeptide collagen.

23. A colored cosmetic composition, comprising:
    1.0 wt % to 6.0 wt % pigment; 1.0 wt % to 50.0 wt % oil; 1.0 wt % to 20.0 wt % wax; and 0.001 wt % to 30.000 wt % marine invertebrate type V telopeptide collagen.

24. A makeup formulation, comprising:
    5.0 wt % to 70.0 wt % oil; 10.0 wt % to 95.0 wt % water; 5.0 wt % to 40.0 wt % pigment, and 0.001 wt % to 30.000 wt % marine invertebrate type V telopeptide collagen.

25. A cosmetic cream, comprising:
    20.0 wt % to 70.0 wt % water; 5.0 wt % to 20.0 wt % emollient; and 0.001 wt % to 30.000 wt % marine invertebrate type V telopeptide collagen.

26. A cosmetic lotion, comprising:
    10.0 wt % to 80.0 wt % water; 5.0 wt % to 20.0 wt % emollient; and 0.001 wt % to 30.000 wt % marine invertebrate type V telopeptide collagen.

27. A colored cosmetic composition, comprising:
    1.0 wt % 6.0 wt % pigment; 0.5 wt % to 30.0 wt % surfactant; 1.0 wt % to 20.0 wt % wax; and 0.001 wt % to 30.000 wt % marine invertebrate type V telopeptide collagen.

28. A makeup formulation, comprising:
    0.1 wt % to 30.0 wt % emollient; 10.0 wt % to 95.0 wt % water; 5.0 wt % to 40.0 wt % pigment, and 0.00 1 wt % to 30.000 wt % marine invertebrate type V telopeptide collagen.

29. A cosmetic composition, comprising
    (a) marine invertebrate type V atelopeptide collagen and
    (b) at least one of an emollient, a wax, or from about 1.3 wt % to 30 wt % surfactant.

* * * * *